(12) United States Patent
Hall

(10) Patent No.: US 7,650,780 B2
(45) Date of Patent: Jan. 26, 2010

(54) TIME-RESOLVED EXHAUST EMISSIONS SENSOR

(75) Inventor: Matthew J. Hall, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 905 days.

(21) Appl. No.: 11/039,365

(22) Filed: Jan. 19, 2005

(65) Prior Publication Data

US 2005/0178675 A1    Aug. 18, 2005

Related U.S. Application Data

(63) Continuation-in-part of application No. PCT/US03/22599, filed on Jul. 18, 2003.

(60) Provisional application No. 60/397,117, filed on Jul. 19, 2002, provisional application No. 60/397,454, filed on Jul. 19, 2002.

(51) Int. Cl.
*G01M 15/10* (2006.01)
(52) U.S. Cl. .................. 73/114.71; 73/23.31
(58) Field of Classification Search ............ 73/23.31, 73/23.32, 114.69, 114.71, 114.72, 114.73, 73/114.75, 114.76
See application file for complete search history.

(56) References Cited

U.S. PATENT DOCUMENTS

| | | | |
|---|---|---|---|
| 2,307,602 A | 1/1943 | Penney | |
| 3,826,574 A | 7/1974 | Brown, Jr. | |
| 4,121,458 A | 10/1978 | Fort | |
| 4,656,832 A | 4/1987 | Hukihisa et al. | |
| 4,713,964 A | 12/1987 | Ioannides | |
| 4,939,466 A * | 7/1990 | Johnson et al. | 324/464 |
| 5,008,628 A | 4/1991 | Krigmont et al. | |
| 5,104,513 A | 4/1992 | Lee et al. | |
| 5,264,272 A | 11/1993 | Tanabe et al. | |
| 5,290,606 A | 3/1994 | Hestevik et al. | |
| 5,302,935 A | 4/1994 | Chatterjee | |
| 5,608,155 A | 3/1997 | Ye et al. | |
| 5,795,454 A | 8/1998 | Friese et al. | |
| 5,892,140 A | 4/1999 | Wood | |
| 5,922,946 A | 7/1999 | Hirota et al. | |

(Continued)

FOREIGN PATENT DOCUMENTS

DE       4236711       5/1993

(Continued)

OTHER PUBLICATIONS

Young, Lee W., "International Search Report", (Aug. 15, 2008),1-3.

(Continued)

*Primary Examiner*—Eric S McCall

(57) ABSTRACT

A sensor may be used to measure particulate mass concentration in the exhaust of an internal combustion engine. The sensor may include a signal electrode and a detector electrode at least partially enclosed within a sensor body. The sensor may continuously measure the particulate mass concentration in the exhaust of the internal combustion engine. Continuously measuring the particulate mass concentration may produce a time-resolved measurement of the particulate mass concentration. In certain embodiments, the sensor may be coupled to a feedback control system that may adjust operating conditions of the internal combustion engine.

39 Claims, 3 Drawing Sheets

U.S. PATENT DOCUMENTS

| | | | |
|---|---|---|---|
| 5,942,190 | A | 8/1999 | Kato et al. |
| 6,076,393 | A | 6/2000 | Kato et al. |
| 6,161,421 | A | 12/2000 | Fang et al. |
| 6,214,208 | B1 | 4/2001 | Ando et al. |
| 6,557,393 | B1 | 5/2003 | Gokhfeld et al. |
| 6,634,210 | B1 | 10/2003 | Bosch et al. |
| 6,705,152 | B2 | 3/2004 | Routkevitch et al. |
| 6,763,699 | B1 | 7/2004 | Hunter et al. |
| 6,971,258 | B2 * | 12/2005 | Rhodes et al. ............. 73/28.01 |
| 7,041,153 | B2 | 5/2006 | Totoki et al. |
| 7,063,731 | B2 | 6/2006 | Roe |
| 7,406,855 | B2 | 8/2008 | Tikkanen et al. |
| 2003/0014966 | A1 * | 1/2003 | Hirota et al. .................. 60/284 |
| 2003/0121251 | A1 * | 7/2003 | Kelley et al. .................. 60/288 |
| 2006/0016246 | A1 * | 1/2006 | Rhodes et al. ............. 73/28.01 |
| 2007/0089399 | A1 * | 4/2007 | Rhodes et al. ................ 60/278 |
| 2007/0271903 | A1 * | 11/2007 | Rhodes et al. ................ 60/278 |
| 2008/0265870 | A1 | 10/2008 | Nair et al. |
| 2009/0056416 | A1 | 3/2009 | Nair et al. |

FOREIGN PATENT DOCUMENTS

| | | |
|---|---|---|
| DE | 19536705 | 3/1997 |
| DE | 19817402 | 9/1999 |
| JP | 60-123757 | 7/1985 |
| JP | 64-20441 | 1/1989 |

OTHER PUBLICATIONS

Young, Lee W., "Written Opinion of the International Searching Authority", (Aug. 15, 2008),1-10.

Young, Lee W., "International Search Report", (Nov. 25, 2008),1-2.

Young, Lee W., "Written Opinion of the International Searching Authority", (Nov. 25, 2008),1-6.

Hauser, "Method for Measuring Particles in Gas Flow e.g. vehicle exhaust", DE19536705, (Apr. 3, 1997),Abstract.

Hauser, "Sensor Device for Quantitative Evaluation of Particles Suspended in Gas Flow, e.g. smoke particles in diesel engine exhaust gas", DE19817402, (Sep. 30, 1999),Abstract.

Moosmueller, et al., "Time Resolved Characterization of Diesel Particulate Emissions", *Environmental Science and Technology*, vol. 35, No. 4, (2001)781-787.

Olsen, Kaj K., "International Search Report", (Feb. 13, 2004),1-5.

Hauser, "English Translation of DE-19536705", (Apr. 3, 1997),1-8.

Hauser, "English Translation of DE-19817402", (Sep. 30, 1999),1-6.

* cited by examiner

TIME-RESOLVED EXHAUST EMISSIONS SENSOR

PRIORITY CLAIM

This application is a continuation-in-part of PCT Application No. PCT/US03/22599 entitled "Time-Resolved Exhaust Emissions Sensor" to Matthew J. Hall, filed on Jul. 18, 2003, which claims the benefits of U.S. Provisional Patent Application No. 60/397,117 entitled "Time-Resolved Exhaust Emissions Sensor" to Matthew J. Hall, filed on Jul. 19, 2002 and U.S. Provisional Patent Application No. 60/397,454 entitled "Time-Resolved Exhaust Emissions Sensor Using Compact Light Scattering" to Matthew J. Hall, filed on Jul. 19, 2002.

U.S. GOVERNMENT INTEREST

This invention was made with government support under Contract No. HL059472 awarded by the National Institute of Health. The government has certain rights in the invention.

BACKGROUND

1. Field of Invention

The present invention relates generally to devices and methods for measuring time-resolved concentration and/or size distribution of particulate matter emitted in the exhaust of an internal combustion engine.

2. Description of Related Art

Internal combustion engines (e.g., diesel engines) typically generate an exhaust flow that contains varying amounts of particulate matter. The amount and size distribution of particulate matter in the exhaust flow tends to vary with engine operating conditions, such as fuel injection timing, injection pressure, or the engine speed to load relationship. Adjustment of these conditions may be useful in reducing particulate matter emissions and particulate matter sizes from the engine. Reducing particulate matter emissions from internal combustion engines is environmentally favorable. Currently, however, no device exists for determining the mass concentration and the size distribution of the particulate matter in the exhaust of an operating engine in the field (e.g., on-board a vehicle) and in real time.

A device for determining the real-time mass concentrations of particulate matter in the exhaust emission of an internal combustion engine may be useful for controlling operation of the engine. For example, time-resolved mass concentration measurements of particulate matter may be used to provide feedback to a control system for adjustment of operating conditions of the engine to reduce the mass concentration of the particulate matter. These time-resolved measurements may also be used to monitor particulate matter emission compliance in the field and/or to calibrate engine operating parameters.

The angular dependence of the intensity of light scattering from an aggregate of particles (e.g., particulate matter) may be used to determine mass concentrations. A device that measures angular dependence of the intensity of light scattering from an aggregate of particles is generally known as a nephelometer. Nephelometers are typically used to measure the size and concentration of particles in gases or liquids. Research grade nephelometers have been used in research environments for measuring mass concentrations in exhaust emissions from engines. Research grade nephelometers, however, are typically large (e.g., about the size of a small refrigerator) and not usable in the field (i.e., on-board a vehicle). The size of a nephelometer may be related to the number of detectors used to measure the scattering intensity at multiple angles. For example, a typical research grade nephelometer uses 36 detectors for measuring scattering intensity at 36 different angles. In addition, research grade nephelometers may include large external laser systems that are not suitable for use in the field.

A device for monitoring mass concentrations and size distributions of particulate matter in the exhaust of an internal combustion engine may be simple, compact, and inexpensive so that the device can be used on the exhaust system of an engine in the field. The device may withstand the severe operating conditions of the exhaust system (e.g., temperature, corrosion, etc.) and be resistant to fouling from particulate matter buildup.

SUMMARY

A sensor may be used to measure mass concentration of particulate matter in exhaust of a combustion device. The sensor may include a signal electrode and a detector electrode at least partially enclosed in a sensor body. In some embodiments, the signal electrode and/or the detector electrode may be enclosed in an insulating material and a conducting tube to reduce or eliminate the temperature sensitivity of the sensor. The insulating material may have a dielectric constant substantially similar to or greater than a dielectric constant of air.

The sensor may be at least partially placed in a flow of exhaust from a combustion device. A voltage may be applied to a signal electrode of the sensor. A detector electrode may be coupled to a detector system that can be used to measure charge accumulated on the detector electrode as particulate matter flows between the electrodes of the sensor or that can measure the current flow to the detector electrode. Charge accumulation or the electrical current on the detector electrode may vary with changes in the mass concentration of the particulate matter. The charge accumulation or electrical current may be converted to an output voltage by the detector system. In some embodiments, an increase in mass concentration of particulate matter in the exhaust may result in an increase in the output voltage of the detector system.

The output voltage of the detector system may be measured continuously for time-resolved measurement of mass concentration of the particulate matter in the exhaust of the combustion device. In some embodiments, the detector system may be coupled to a feedback control system that operates the combustion device. Operating conditions of the combustion device may be adjusted by the feedback control system to reduce mass concentration of particulate matter in the exhaust.

In certain embodiments, a device may be used to measure mass concentrations and size distributions of particulate matter in the exhaust emission of a combustion engine in real-time and in the field (e.g., on-board a vehicle). The device may include a cylinder section that may be coupled to an exhaust conduit of the combustion engine. A light source may be coupled to the perimeter of the cylinder section. The light source may be compact and relatively inexpensive. In an embodiment, the light source is a diode laser.

A selected number of detectors (e.g., 1 to 6) may be coupled to the perimeter of the cylinder section. The detectors may be photodetectors (e.g., photodiodes, avalanche photodiodes, or photomultipliers). In an embodiment, the photodetectors are placed at various selected angles with respect to the light source. The various angles of the photodetectors may be selected to provide a relatively good estimate of particulate matter size. In certain embodiments, the angles may be selected based on theoretical scattering profiles of light. The theoretical scattering profiles may be determined based upon a particle size distribution, refractive index of particles, and a wavelength of light. For example, in one embodiment, three photodetectors may be placed at angles of about 20°, about 35°, and about 70° with respect to the light source based upon the theoretical scattering profiles.

An electronics system may be coupled to the light source and the detectors. The electronics system may provide power to the light source and the detectors and/or obtain data from the detectors. The electronics system may process the data from the detectors to determine mass concentrations and size distributions of particulate matter. The electronics system may continuously monitor mass concentrations and size distributions in real-time. Operating parameters of the combustion engine may be modified based upon the measurements of mass concentrations and size distributions. The operating parameters may be modified to calibrate the engine or to comply with emission requirements.

In certain embodiments, a flow of gas (e.g., air) may be provided to optical surfaces of the detectors and the light source to inhibit particulate matter contamination of the optical surfaces. In an embodiment, a compressor coupled to the cylinder section may be used to provide the flow of gas.

BRIEF DESCRIPTION OF THE DRAWINGS

Advantages of the present invention may become apparent to those skilled in the art with the benefit of the following detailed description and upon reference to the accompanying drawings in which.

Figure 1:
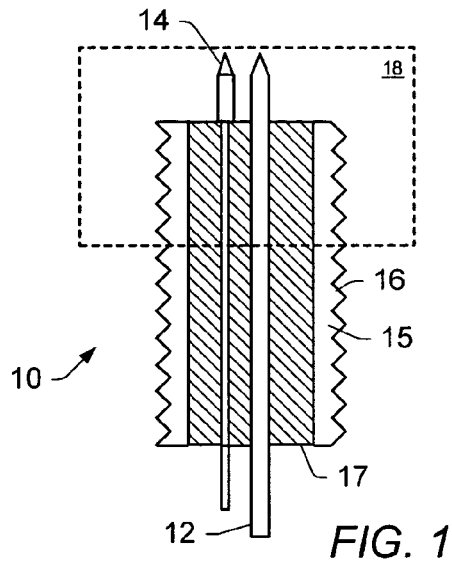
FIG. 1 depicts a sectional front view of an embodiment of a sensor.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION

Figure 2:
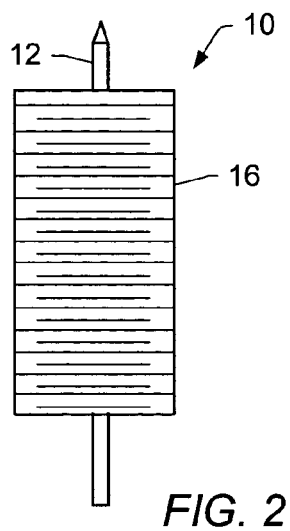
FIG. 2 depicts a side view of an embodiment of a sensor.
Figure 3:
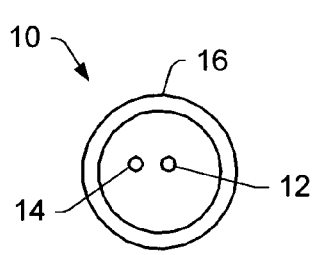
FIG. 3 depicts a top view of an embodiment of a sensor.

FIG. 1 depicts a sectional front view of an embodiment of sensor 10. FIG. 2 depicts a side view of sensor 10 and FIG. 3 depicts a top view of sensor 10. Sensor 10 may be sized such that the sensor may be placed in an exhaust system of an internal combustion engine. For example, sensor 10 may be about the size of an oxygen sensor or a spark plug. A size of sensor 10 may be adjusted for different exhaust systems and/or internal combustion engines. Sensor 10 may include signal electrode 12 and detector electrode 14. Signal electrode 12 and detector electrode 14 may be partially enclosed in sensor body 16. Sensor body 16 may include electrically insulating material that electrically insulates signal electrode 12 and detector electrode 14. Sensor body 16 may include a high temperature, electrically insulating material that is able to withstand the relatively high temperatures of the exhaust of an internal combustion engine (e.g., between about 200° C. and about 1000° C.). Sensor body 16 may include metal housing 15 supporting insulating body 17. In certain embodiments, metal housing 15 may be threaded for threading into an exhaust conduit. In an embodiment, metal housing 15 is a threaded steel housing supporting cold-weld polymer insulating body 17.

In certain embodiments, signal electrode 12 and detector electrode 14 may be spaced apart by a distance of between about 0.05 cm and about 1.5 cm. In one embodiment, a distance between signal electrode 12 and detector electrode 14 is about 0.4 cm. The distance between the electrodes may vary, however. For example, the distance between the electrodes may be varied based upon a desired sensitivity for sensor 10 and/or a selected use of the sensor (e.g., engine type, exhaust volume, etc.).

In an embodiment, signal electrode 12 is a high voltage electrode. Signal electrode 12 may be operable up to 1500 volts. Signal electrode 12 may also be operable in a range of 400 volts to 1200 volts or, in one embodiment, a range of 500 volts to 1000 volts. Signal electrode 12 may include high voltage materials such as copper, aluminum, platinum, etc. A diameter of signal electrode 12 may be selected based on factors such as, but not limited to, an operating voltage range and/or current range of the signal electrode. The diameter of signal electrode 12 is typically between about 0.02 cm and about 0.5 cm. In one embodiment, signal electrode 12 is a copper electrode of about 0.1 cm diameter.

Detector electrode 14 may be used to detect charge or electrical current produced in an exhaust system. Detector electrode 14 may be any electrode capable of collecting and conducting an electrical signal. For example, detector electrode 14 may include materials such as copper, aluminum, platinum, etc. A diameter of detector electrode 14 may be selected based on factors such as, but not limited to, a desired sensitivity of the detector electrode or an operating range (i.e., voltage range or current range) of the detector electrode. The diameter of detector electrode 14 is typically between about 0.02 cm and about 0.5 cm. In an embodiment, detector electrode 14 is a copper electrode with a diameter of about 0.1 cm.

In certain embodiments, sensor 10 may be placed in an exhaust system of an internal combustion engine (e.g., a diesel engine) or other similar combustion device to detect particulate emissions from the combustion device. Sensor 10 may be simple to build, simple to use, compact, and durable. Sensor 10 may be operable without fouling typically caused by accumulation of particulate matter in an exhaust sensor.

Figure 3A:
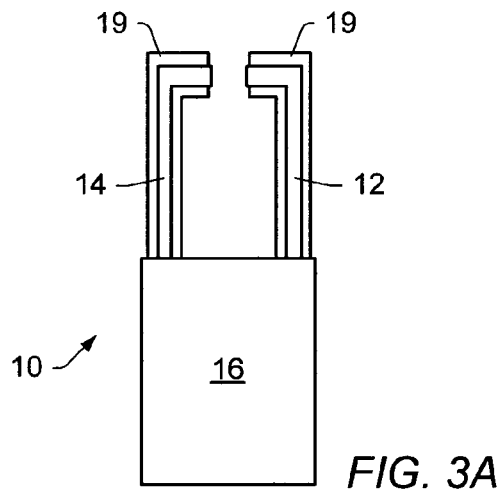
FIG. 3A depicts a front view of an embodiment of a sensor.

In certain embodiments, one or more electrodes may be at least partially enclosed in a sheath (e.g., an electrically insulating sheath) to increase the resistance of a sensor to fouling. FIG. 3A depicts a front view of an embodiment of sensor 10. Signal electrode 12 and/or detector electrode 14 may be at least partially enclosed in sheath 19. In certain embodiments, sheath 19 may enclose all but the tips of signal electrode 12 and detector electrode 14. In such embodiments, a region or volume is formed between an uncovered tip of signal electrode 12 and an uncovered tip of detector electrode 14. In this region or volume, an electrical measurement between the electrodes may be made. In certain embodiments, sheath 19 may be made of electrically insulating material such as plastic (e.g., Teflon®).

Figure 4:
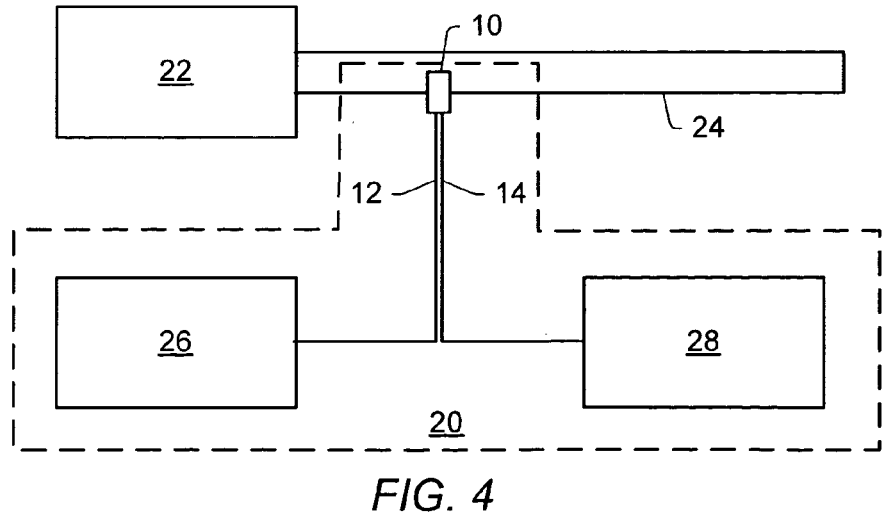
FIG. 4 depicts a schematic representation of an embodiment for detecting particulate matter with a sensor.

FIG. 4 depicts a schematic representation of an embodiment of system 20 for detecting particulate emissions from combustion device 22 with sensor 10. Combustion device 22 may be an internal combustion engine or any other similar engine or combustion device. For example, combustion device 22 may be an automobile or truck diesel engine. In some embodiments, sensor 10 may be coupled to the exhaust of a burner or a furnace.

Exhaust conduit 24 may be coupled to combustion device 22. Exhaust conduit 24 may be an exhaust pipe of combustion device 22. Sensor 10 may be coupled to exhaust conduit 24. Sensor 10 may be coupled to exhaust conduit 24 such that sensor head 18 (shown in FIG. 1) lies in the exhaust conduit. Sensor 10 may be coupled to exhaust conduit 24 at any desired location along the exhaust conduit. The location of sensor 10 along exhaust conduit 24 may be selected, for example, to provide a desired sensitivity or to locate the sensor such that an operating temperature of the sensor does not exceed a maximum selected temperature (e.g., a maximum operating temperature of materials in the sensor).

An end of signal electrode 12 on sensor 10 located externally to exhaust conduit 24 may be coupled to voltage supply 26. Voltage supply 26 may be a high voltage power supply or other device capable of supplying high voltage to signal electrode 12. Voltage supply 26 may also operate at low current for low power consumption. In an embodiment, voltage supply 26 is capable of providing a voltage up to 1500 volts to signal electrode 12. In certain embodiments, voltage supply 26 provides a voltage that is lower than a voltage that may create a spark breakdown between the electrodes. The voltage supplied to signal electrode 12 may be a positive or negative bias voltage. In certain embodiments, voltage supply 26 provides a positive voltage between 500 volts and 1000 volts to signal electrode 12. In an embodiment, voltage supply 26 provides a constant voltage to signal electrode 12.

An end of detector electrode 14 on sensor 10 located externally to exhaust conduit 24 may be coupled to detector system 28. In some embodiments, detector electrode 14 may be grounded. Detector system 28 may be an electronic system used to measure charge accumulation or current flow on detector electrode 14. In an embodiment, detector system 28 is a charge amplifier system that measures the accumulation of charge or the current flow on detector electrode 14. Detector system 28 may convert the charge accumulation or the current flow measured on detector electrode 14 into an output voltage. Detector system 28 may produce changes in voltage as the charge accumulation or the current flow from particulate matter increases or decreases on detector electrode 14. As particulate matter flow increases through sensor 10 in exhaust conduit 24, charge accumulation or current flow (i.e., the output voltage of detector system 28) may increase. The charge accumulation or the current flow in sensor 10 may be affected by a change in dielectric constant between signal electrode 12 and detector electrode 14 produced by the flow of particulate mass between the electrodes. The charge accumulation or the current flow in sensor 10 may also be due to the presence of carbon ions produced from the ionization of particulate matter by the high voltage electric field between the electrodes. In general, detector electrode 14 may be operated in a similar manner to a detector electrode used in a hydrocarbon flame-ionization detector (FID). In some embodiments, a spark discharge (e.g., a spark plug) may be placed in exhaust conduit 24 to generate a discharge and ionize the particulate matter for detection in sensor 10.

The output voltage of detector system 28 tends to vary with variations in mass concentration at sensor 10. Thus, a particular voltage output may correspond to an individual mass concentration. Voltage output of detector system 28 may be calibrated versus mass concentration to determine a correlation between voltage output and mass concentration for the sensor.

In an embodiment, the voltage output of detector system 28 may be monitored continuously. Consumption of power during continuous monitoring may be kept relatively low because of the constant voltage at signal electrode 12 and the low current flow through sensor 10. Continuous monitoring of the voltage (i.e., mass concentration) may allow for time-resolved measurement of the mass concentration. Time-resolved measurement may allow for detection of trends in the mass concentration of particulate matter. In other embodiments, mass concentration measurements may not be time resolved (e.g., measurements may include total mass over a length of time, concentration at a singular point in time, etc.).

In certain embodiments, detector system 28 may be coupled to a feedback control system for operating combustion device 22. Operating conditions of combustion device 22 may be adjusted based on the mass concentration of the particulate matter measured by detector system 28. Operating conditions may be adjusted to reduce the mass concentration of the particulate matter if the mass concentration exceeds a selected value. For example, operating conditions such as fuel injection timing, injection pressure, and/or an engine speed/load relationship may be adjusted to reduce the mass concentration. In some embodiments, these conditions may be adjusted or refined to produce a desired low mass concentration of particulate matter as detected by sensor 10.

In some embodiments, sensor 10 may be temperature sensitive. Sensor 10 may be temperature sensitive such that an output voltage of the sensor (as determined by detector system 28) drifts to an offset value at higher temperatures. The output voltage may drift to a maximum offset value and remain at the maximum offset value at a certain increased temperature. In certain embodiments, the temperature dependence of sensor 10 may be compensated for through calibration (e.g., temperature versus voltage offset correlation measurements) or other compensation methods.

The temperature sensitivity of sensor 10 may be reduced or eliminated by covering or shielding signal electrode 12 and/or detector electrode 14. In an embodiment, an insulating material with a dielectric constant substantially similar to or greater than air (e.g., greater than about 1.0) may be placed around signal electrode 12 and/or detector electrode 14. In the insulating material, signal electrode 12 and/or detector electrode 14 may be further placed in conducting tubes (e.g., copper tubes). Shielding signal electrode 12 and/or detector electrode 14 with the insulating material and the conducting tubes may reduce or eliminate the temperature sensitivity of sensor 10.

In an experiment, an exhaust plume from a sooting acetylene flame was drawn through a 5-inch diameter metal duct. The flow of exhaust was drawn by a vacuum system attached to the end of the metal duct. Sensor 10 was coupled to the metal duct such that sensor head 18 was in the flow of exhaust. Sensor 10 was charged with a voltage of between 500 volts and 1000 volts using a high voltage power supply. A strong voltage signal was observed on an oscilloscope coupled to sensor 10 when a particulate stream was introduced into the exhaust flow. When the particulate stream was reduced or removed from the exhaust flow, the voltage signal decreased to a minimum value.

In another experiment, sensor 10 was placed in a flow of exhaust generated by a diesel engine. Sensor 10 was found to be sensitive to the temperatures generated in a diesel engine exhaust. Shielding of signal electrode 12 and detector electrode 14, as described above, appeared to eliminate the temperature sensitivity of the sensor.

Figure 5:
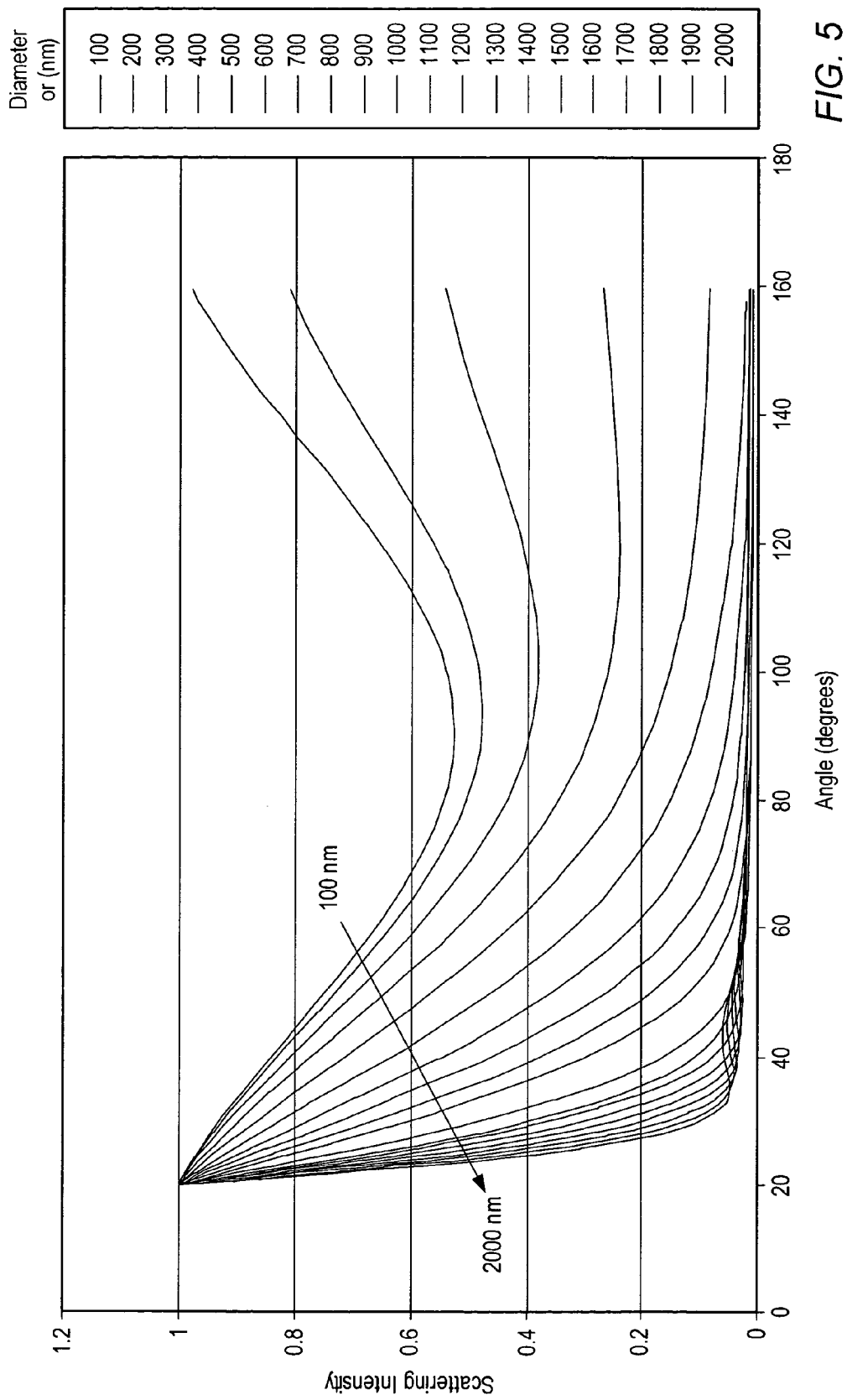
FIG. 5 depicts a plot of theoretical scattering intensity versus angle for detection of several particle sizes.

In certain embodiments, light scattering may be used to measure size distribution of particulate matter in exhaust emission of a combustion engine. FIG. 5 depicts a plot of theoretical Mie scattering profiles for a laser wavelength of 1064 nm and spherical particles with a refractive index of 1.60. The refractive index of 1.60 is typical for particulate matter (e.g., soot) found in exhaust systems of internal combustion engines. Scattering intensity is shown versus angle of detection for various mean particle diameters. The theoretical curves in FIG. 5 are for a log-normal distribution of particle sizes with a 0.05 standard deviation. Log-normal distributions of particle sizes have been shown to be typical in internal combustion engine exhaust emissions. The theoretical curves are relatively unaffected by the width of the particle distribution (i.e., standard deviations larger than 0.05).

The theoretical curves in FIG. 5 show that using smaller numbers of detectors may provide a good estimate of particulate matter size. For example, three detectors placed at scattering angles of about 20°, about 35°, and about 70° may allow a relatively good estimation of particulate matter size distributions in an engine exhaust emission for a laser wavelength of 1064 nm and particulate matter with a refractive index of soot. Using these three angles may provide a good cross-section of scattering curves shown in FIG. 5. Other small numbers of detectors (e.g., 4 or 5) may also be used to provide an estimate of particulate matter size distributions. The number of detectors needed and/or the angles of detection may vary depending on factors such as, but not limited to, a selected laser wavelength, types of particles being measured, a desired sensitivity of the measurement, or a desired accuracy in particle size measurement.

The mass concentration of particulate matter in an exhaust emission may be correlated with the absolute intensity of the scattered light (i.e., the absolute intensity of scattered light at all detection angles). Calibration for the variation of absolute intensity of the scattered light with mass concentration of particulate matter may be done using another technique that measures mass concentration. For example, values of the absolute intensity of scattered light may be correlated to values of mass concentration measured with another device simultaneously.

Figure 6:
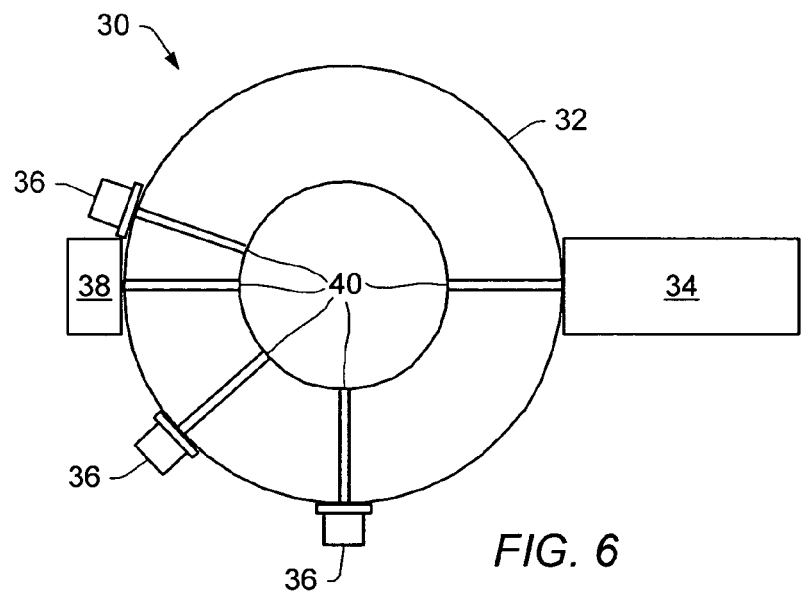
FIG. 6 depicts a side view of an embodiment of a sensor.
Figure 7:
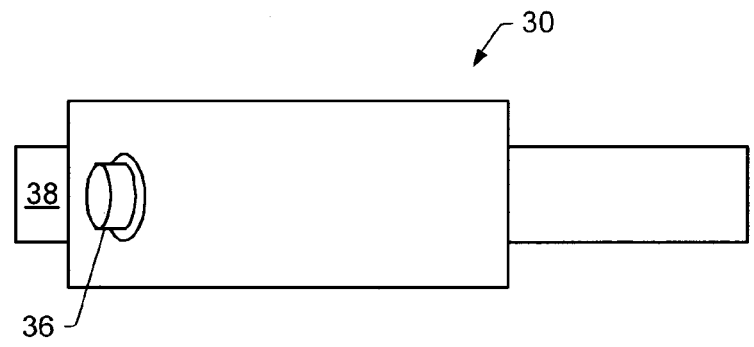
FIG. 7 depicts a top view of an embodiment of a sensor.

FIG. 6 depicts a side view of an embodiment of sensor 30 that may be used to determine mass concentrations and size distributions of particulate matter from an engine exhaust emission in the field. FIG. 7 depicts a top view of sensor 30. Sensor 30 may include cylinder section 32. Cylinder section 32 may be a cylindrical section that is configured to couple axially to an exhaust conduit of a combustion engine. In an embodiment, cylinder section 32 is an adaptor pipe for coupling to an exhaust pipe of a combustion engine. In certain embodiments, cylinder section 32 may be a test section configured to be a portion of an exhaust conduit of a combustion engine. Cylinder section 32 generally has a bore diameter substantially similar to the diameter of an exhaust conduit for coupling to the exhaust conduit. A typical bore diameter of cylinder section 32 is about 5 cm.

Light source 34 may be coupled to the perimeter of cylinder section 32. Light source 34 may be a laser. Light source 34 may be capable of producing light at a selected wavelength (e.g., 1064 nm or any other suitable wavelength) or in a range of wavelengths (e.g., between about 400 nm and 2 μm). The wavelength of light source 34 may be selected based on, for example, an expected size distribution of particulate matter in cylinder section 32. In an embodiment, light source 34 is a diode laser. Generally, light source 34 is a compact, durable light source that is operable in a field testing environment.

One or more detectors 36 may be coupled to the perimeter of cylinder section 32. In certain embodiments, three or more detectors 36 are coupled to the perimeter of cylinder section 32. In one embodiment, as shown in FIG. 6, three detectors 36 are coupled to the perimeter of cylinder section 32. The number of detectors 36 may be selected based upon factors such as, but not limited to, a particle size detection range of sensor 30 or a desired sensitivity of the sensor.

In an embodiment, detectors 36 are placed at various selected scattering angles from light source 34. The scattering angles may be selected to provide a relatively good estimate of particulate matter size based upon scattering profiles for a log-normal particulate matter size distribution. For example, the scattering angles may be selected based on the theoretical Mie scattering profiles depicted in FIG. 5. The scattering profiles may be dependent on such factors as the wavelength of light source 34, the index of refraction of particulate matter detected by sensor 30, and/or the distribution pattern (e.g., the type of distribution (e.g., log-normal), the width of the distribution, or the standard deviation of the distribution) of particulate matter sizes. Various theoretical scattering profiles may be generated for varying attributes of a detection system or combustion engine and the scattering angles of detectors 36 may be chosen accordingly. In an embodiment, three detectors 36 may be placed at angles of about 20°, about 35°, and about 70° from light source 34.

Detectors 36 may include any type of detector that measures light intensity at a wavelength of light source 34 or in the range of wavelengths of the light source. In certain embodiments, detectors 36 may include photodiodes, avalanche photodiodes, and/or photomultipliers.

In some embodiments, more than one light source may be used in sensor 30. Multiple light sources may be used to determine particulate matter size distributions over a wider range of size distributions. Multiple light sources may be placed at various angles along the perimeter of cylinder section 32. Detectors 36 could be used for one light source or more than one light source depending on the scattering angle of the detectors and/or the sensitivity of the detectors to each wavelength of light.

In an embodiment, beam dump 38 may be coupled to the perimeter of cylinder section 32 substantially 180° from light source 34. Beam dump 38 may be used to collect extraneous light in cylinder section 32 and to inhibit multiple scattering in cylinder section 32. In certain embodiments, beam dump 38 may be a light power meter (e.g., a laser power meter) used to measure light attenuation in cylinder section 32. The measurement of light attenuation in cylinder section 32 may be used to determine light absorption by particles in the cylinder section.

Light source 34, detectors 36, and beam dump 38 may be aligned in a single plane around the perimeter of cylinder section 32. Light source 34, detectors 36, and beam dump 38 are typically arranged to provide maximum sensitivity for light detection with minimal back-scattering of light in cylinder section 32. Holes 40 may be formed in cylinder section 32 to allow light to propagate out of light source 34 and into detectors 36 and beam dump 38. Holes 40 may be rectangular or circular shaped holes formed in cylinder section 32. Holes 40 may have a cross-sectional area selected to allow the wavelength, or range of wavelengths, of light from light source 34 to propagate in the holes.

In some embodiments, conduits (e.g., tubes) may be coupled to holes 40 and extended into cylinder section 32. The conduits may be coupled to holes 40 for detectors 36. The conduits may be extended into cylinder section 32 to minimize attenuation of light scattering from particles in the cylinder section.

Figure 8:
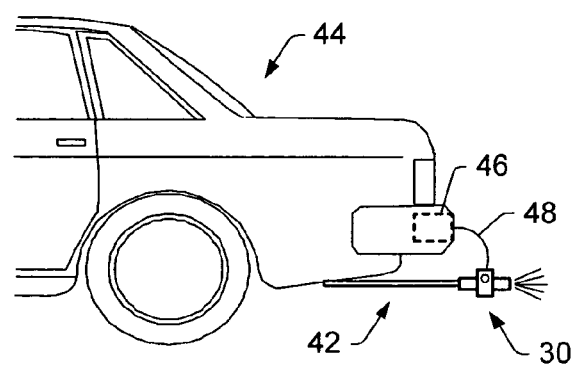
FIG. 8 depicts a representation of an embodiment for on-board monitoring of emissions from a vehicle exhaust.

FIG. 8 depicts a representation of an embodiment for on-board monitoring of emissions from a vehicle exhaust using sensor 30. Sensor 30 may be coupled to exhaust conduit 42 of vehicle 44. Exhaust conduit 42 may be coupled to an engine of vehicle 44. In certain embodiments, the engine is a diesel engine. For example, the engine may be a production diesel engine or a direct injection spark ignition engine. In some embodiments, sensor 30 may be used to determine particle size and/or distribution from nanoparticle production devices.

Electronics system 46 may be coupled to sensor 30. Electronics system 46 may be coupled to sensor 30 with wires 48. Wires 48 may include power and/or signal wires for light source 34 and detectors 36. Electronics system 46 may include electronics to power light source 34 and detectors 36, and electronics to obtain and process data from detectors 36. In some embodiments, the electronics to power light source 34, the electronics to power detectors 36, and the electronics to obtain and process data from detectors 36 may be located in two or more different electronics systems.

In an embodiment, electronics system 46 is located in vehicle 44. In other embodiments, electronics system 46 may be located external to vehicle 44. For example, electronics system 46 may be located on an apparatus (e.g., a transportable apparatus such as a cart) that may be moved from one vehicle to another and/or located between two or more vehicles. An electronics system located on such an apparatus may be coupled to more than one sensor 30 either consecutively or simultaneously.

Electronics system 46 may be used to process data from detectors 36 and characterize particulate matter emissions from the engine of vehicle 44. This data may be used to adjust operating parameters of the engine to control emissions (e.g., reduce the mass concentration and/or the particulate matter size) from vehicle 44. In an embodiment, electronics system 46 may be used to characterize particulate matter emissions from the engine of vehicle 40 during actual use of the engine. Operating parameters (e.g., fuel injection timing, injection pressure, an engine speed/load relationship, etc.) of the engine may be modified based on the characterization of particulate matter emissions provided by sensor 30 and electronics system 46. The operating parameters may be modified to calibrate the engine of vehicle 44. In certain embodiments, the operating parameters are modified to comply with emission requirements (e.g., government environmental emission regulations or guidelines).

In an embodiment, sensor 30 and electronics system 46 may continuously monitor particulate matter emissions from vehicle 44. Continuous monitoring of particulate matter emissions may allow for real-time and/or time-resolved measurement of the particulate matter mass concentration and particulate matter size distribution in the field (i.e., on-board vehicle 44). Time-resolved measurement may allow for detection of trends in the particulate matter mass concentration and/or size distribution. In other embodiments, the particulate matter mass concentration and/or size distribution may be measured on a non time-resolved basis, if so desired. Sensor 30 and electronics system 46 may provide a simple, compact, low cost method for real-time monitoring of particulate matter mass concentrations and size distributions in the emissions of a vehicle.

In some embodiments, a gas (e.g., air) may be allowed to flow along optical surfaces in cylinder section 32. The flow of gas may keep the optical surfaces substantially free of particulate matter contamination. In an embodiment, the gas may be allowed to flow into through holes 40 of cylinder section 32. In certain embodiments, a compressor may be used to provide the flow of gas. The compressor may be small and compact so that the compressor may be coupled to the perimeter of cylinder section 32.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A device for measuring mass concentration of particulate matter in an exhaust flow of an internal combustion engine, comprising:
    a sensor body, wherein the sensor body is configured to be coupled to an exhaust conduit of the internal combustion engine;
    a signal electrode and a detector electrode at least partially enclosed in the sensor body, wherein an end of the signal electrode and an end of the detector electrode are configured to be located in the exhaust conduit; and
    wherein a voltage is applied to the signal electrode during use and an electric charge accumulates on the detector electrode as particulate matter flows between the ends of the signal electrode and the detector electrode in the exhaust conduit during use, and wherein the electric charge that accumulates on the detector electrode varies with the mass concentration of particulate matter in the exhaust conduit.

2. The device of claim 1, wherein the signal electrode is at least partially enclosed in an insulating material and a conducting tube.

3. The device of claim 1, wherein the detector electrode is at least partially enclosed in an insulating material and a conducting tube.

4. The device of claim 1, wherein the voltage applied to the signal electrode during use is between about 500 volts and about 1000 volts.

5. The device of claim 1, wherein the detector electrode is coupled to a detector system that converts the electric charge that accumulates on the detector electrode into an output voltage, and wherein the output voltage corresponds to the mass concentration of particulate matter in the exhaust conduit.

6. The device of claim 1, further comprising an electrically insulating sheath at least partially enclosing the signal electrode and an electrically insulating sheath at least partially enclosing the detector electrode.

7. A system for measuring mass concentration of particulate matter in an exhaust flow of an internal combustion engine, comprising:
    a sensor body, wherein the sensor body is configured to be coupled to an exhaust conduit of the internal combustion engine;

a signal electrode and a detector electrode at least partially enclosed in the sensor body, wherein an end of the signal electrode and an end of the detector electrode are configured to be located in the exhaust conduit;

a voltage supply coupled to the signal electrode; and a detector system coupled to the detector electrode;

wherein a voltage is applied to the signal electrode from the voltage supply during use and an electric charge accumulates on the detector electrode as particulate matter flows between the ends of the signal electrode and the detector electrode in the exhaust conduit during use, and wherein the electric charge that accumulates on the detector electrode varies with the mass concentration of particulate matter in the exhaust conduit.

8. The system of claim 7, wherein the signal electrode is at least partially enclosed in an insulating material and a conducting tube.

9. The system of claim 7, wherein the detector electrode is at least partially enclosed in an insulating material and a conducting tube.

10. The system of claim 7, wherein the voltage applied to the signal electrode during use is between about 500 volts and about 1000 volts.

11. The system of claim 7, wherein the detector system converts the electric charge that accumulates on the detector electrode into an output voltage, and wherein the output voltage corresponds to the mass concentration of the particulate matter in the exhaust conduit.

12. The system of claim 7, further comprising an electrically insulating sheath at least partially enclosing the signal electrode and an electrically insulating sheath at least partially enclosing the detector electrode.

13. A method for measuring mass concentration of particulate matter in an exhaust conduit of an internal combustion engine, comprising:

applying a voltage to a signal electrode, wherein an end of the signal electrode is located in the exhaust conduit;

measuring an accumulation of electric charge on a detector electrode, wherein an end of the detector electrode is located in the exhaust conduit, and wherein the accumulation of electric charge varies with the mass concentration of particulate matter in the exhaust conduit; and converting the accumulation of electric charge on the detector electrode to an output voltage, wherein the output voltage corresponds to the mass concentration of particulate matter in the exhaust conduit.

14. The method of claim 13, wherein the signal electrode and the detector electrode are at least partially enclosed in a sensor body.

15. The method of claim 13, wherein the signal electrode is at least partially enclosed in an insulating material and a conducting tube.

16. The method of claim 13, wherein the detector electrode is at least partially enclosed in an insulating material and a conducting tube.

17. The method of claim 13, wherein the voltage applied to the signal electrode is between about 500 volts and about 1000 volts.

18. A system to detect particulate matter in a flow of gas, the system comprising:

a detector electrode configured to at least partially extend into the flow of gas, wherein the detector electrode is configured to accumulate a charge in response to a stream of particulate matter within the flow of gas;

a charge amplifier coupled to the detector electrode, wherein the charge amplifier is configured to be located at least partially within the flow of gas to allow the stream of particulate matter to flow between ends of the signal electrode and the detector electrode, and wherein the charge amplifier is further configured to generate an output voltage corresponding to the charge accumulated on the detector electrode, wherein the output voltage of the charge amplifier is calibrated to a mass concentration of the particulate matter within the flow of gas; and a signal electrode, wherein the signal electrode is configured to be located at least partially within the flow of gas to allow the stream of particulate matter to flow between ends of the signal electrode and the detector electrode.

19. The system of claim 18, wherein the detector electrode and the signal electrode are separated by a distance of about 0.05 cm to 1.5 cm between the detector electrode and the signal electrode.

20. The system of claim 18, further comprising:

sheaths to at least partially enclose the detector electrode and the signal electrode, wherein the sheaths allow tips of the detector electrode and the signal electrode to be exposed;

a sensor body configured to at least partially enclose the detector electrode and the signal electrode, wherein the sensor body comprises:

a metal housing; and an insulating body within the metal housing, wherein the insulating body is configured to insulate portions of the detector electrode and the signal electrode enclosed by the sensor body; and a conducting tube located within the insulating body of the sensor body, wherein the conducting tube is configured to at least partially shield the detector electrode and the signal electrode from high temperatures of the flow of gas.

21. The system of claim 18, wherein the diameter of the detector electrode and the diameter of the signal electrode are between about 0.02 cm to 0.5 cm.

22. The system of claim 18, further comprising a voltage supply coupled to the signal electrode, wherein the voltage supply is configured to supply a voltage on the signal electrode.

23. The system of claim 22, wherein the voltage supply is configured to supply a high voltage of up to about 1500 volts on the signal electrode.

24. The system of claim 22, wherein the voltage supply is configured to supply a high voltage of between about 400 volts to 1200 volts on the signal electrode.

25. The system of claim 22, wherein the voltage supply is configured to supply a high voltage of between about 500 volts to 1000 volts on the signal electrode.

26. The system of claim 22, wherein the stream of particulate matter between the signal electrode and the detector electrode changes a dielectric constant between the signal electrode and the detector electrode, wherein the change in the dielectric constant facilitates the accumulation of charge on the detector electrode.

27. The system of claim 22, further comprising a spark discharge to generate a discharge and ionize the particulate matter within the stream of particulate matter between the signal electrode and the detector electrode to produce carbon ions, wherein the carbon ions between the signal electrode and the detector electrode change the accumulation of charge on the detector electrode.

28. A method for measuring mass concentration of particulate matter in a flow of gas, the method comprising:

accumulating a charge on a detector electrode which at least partially extends into the flow of gas in response to a stream of particulate matter within the flow of gas; and generating an output voltage at a charge amplifier, wherein the output voltage corresponds to the charge accumulated on the detector electrode;

determining a mass concentration of the particulate matter within the flow of gas based on the output voltage; and supplying a voltage on a signal electrode located at least partially within the flow of gas, wherein the detector electrode and the signal electrode are separated by a distance to allow the stream of particulate matter to flow between ends of the detector electrode and the signal electrode.

29. The method of claim 28, wherein supplying the voltage to the signal electrode further comprises supplying a high voltage of up to about 1500 volts on the signal electrode.

30. The method of claim 28, wherein supplying the voltage to the signal electrode further comprises supplying a high voltage of between about 400 volts to 1200 volts on the signal electrode.

31. The method of claim 28, wherein supplying the voltage to the signal electrode further comprises supplying a high voltage of between about 500 volts to 1000 volts on the signal electrode.

32. The method of claim 28, wherein the stream of particulate matter between the signal electrode and the detector electrode changes a dielectric constant between the signal electrode and the detector electrode, wherein the change in the dielectric constant facilitates the accumulation of charge on the detector electrode.

33. The method of claim 28, further comprising generating a discharge to ionize the particulate matter within the stream of particulate matter between the signal electrode and the detector electrode to produce carbon ions, wherein the carbon ions between the signal electrode and the detector electrode change the accumulation of charge on the detector electrode.

34. The method of claim 28, further comprising at least partially insulating the signal electrode and the detector electrode.

35. The method of claim 28, further comprising adjusting an operating condition of a combustion device to reduce the mass concentration of the particulate matter.

36. The method of claim 28, further comprising:
monitoring the output voltage of the charge amplifier; and
generating a time-resolved measurement of the mass concentration of the particulate matter.

37. The method of claim 28, further comprising:
monitoring the output voltage of the charge amplifier; and
generating a measurement, other than a time-resolved measurement, of the mass concentration of the particulate matter.

38. A system to detect particulate matter in a flow of gas, the system comprising:

a detector electrode configured to at least partially extend into the flow of gas, wherein the detector electrode is configured to accumulate a charge in response to a stream of particulate matter within the flow of gas;

a charge amplifier coupled to the detector electrode, wherein the charge amplifier is configured to be located at least partially within the flow of gas to allow the stream of particulate matter to flow between ends of the signal electrode and the detector electrode, and wherein the charge amplifier is further configured to generate an output voltage corresponding to the charge accumulated on the detector electrode, wherein the output voltage of the charge amplifier is calibrated to a mass concentration of the particulate matter within the flow of gas; and a feedback control system coupled to the charge amplifier, wherein the feedback control system is configured to adjust an operating condition of the combustion device to reduce the mass concentration of the particulate matter in the exhaust stream, and wherein the feedback control system is further configured to monitor the output voltage of the charge amplifier to generate a time-resolved measurement of the mass concentration of the particulate matter in the exhaust stream.

39. A system to detect particulate matter in a flow of gas, the system comprising:

a detector electrode configured to at least partially extend into the flow of gas, wherein the detector electrode is configured to accumulate a charge in response to a stream of particulate matter within the flow of gas;

a charge amplifier coupled to the detector electrode, wherein the charge amplifier is configured to be located at least partially within the flow of gas to allow the stream of particulate matter to flow between ends of the signal electrode and the detector electrode, and wherein the charge amplifier is further configured to generate an output voltage corresponding to the charge accumulated on the detector electrode, wherein the output voltage of the charge amplifier is calibrated to a mass concentration of the particulate matter within the flow of gas; and a feedback control system coupled to the charge amplifier, wherein the feedback control system is configured to adjust an operating condition of the combustion device to reduce the mass concentration of the particulate matter in the exhaust stream, and wherein the feedback control system is further configured to monitor the output voltage of the charge amplifier to generate a measurement, other than a time-resolved measurement, of the mass concentration of the particulate matter in the exhaust stream.

* * * * *